United States Patent
Meyer

(10) Patent No.: US 7,964,644 B2
(45) Date of Patent: *Jun. 21, 2011

(54) USE OF NEUROTOXIC SUBSTANCES FOR THE PRODUCTION OF A MEANS FOR THE TREATMENT OF JOINT PAINT AND METHOD FOR APPLICATION OF SAID MEANS

(75) Inventor: Dominik Meyer, Zürich (CH)

(73) Assignee: MESTEX AG, Zurich (CH)

( * ) Notice: Subject to any disclaimer, the term of this patent is extended or adjusted under 35 U.S.C. 154(b) by 1368 days.

This patent is subject to a terminal disclaimer.

(21) Appl. No.: 10/521,599

(22) PCT Filed: Jul. 19, 2002

(86) PCT No.: PCT/CH02/00400
§ 371 (c)(1),
(2), (4) Date: Jan. 18, 2005

(87) PCT Pub. No.: WO2004/009064
PCT Pub. Date: Jan. 29, 2004

(65) Prior Publication Data
US 2005/0215633 A1    Sep. 29, 2005

(51) Int. Cl.
*A61K 31/167*    (2006.01)
*A61K 31/16*    (2006.01)
*A61K 33/02*    (2006.01)
*A61K 33/04*    (2006.01)
*A61K 51/00*    (2006.01)
*A01N 29/04*    (2006.01)
*A01N 59/02*    (2006.01)
*A01N 59/00*    (2006.01)
*A01N 37/18*    (2006.01)
*A01N 33/24*    (2006.01)

(52) U.S. Cl. ........ 514/613; 514/741; 514/751; 514/818; 424/1.11; 424/703; 424/722

(58) Field of Classification Search .......... None
See application file for complete search history.

(56) References Cited

U.S. PATENT DOCUMENTS

| 3,368,937 | A |   | 2/1968  | Macek et al. |
| 3,917,830 | A | * | 11/1975 | Pearce et al. .................. 514/171 |
| 4,296,104 | A | * | 10/1981 | Herschler ..................... 424/679 |
| 4,657,764 | A |   | 4/1987  | Arias-Alvarez |
| 4,851,442 | A |   | 7/1989  | Watson |
| 5,242,683 | A | * | 9/1993  | Klaveness ..................... 424/9.35 |
| 5,942,241 | A | * | 8/1999  | Chasin et al. ................. 424/426 |
| 6,248,345 | B1 |  | 6/2001  | Goldenheim et al. |
| 6,261,547 | B1 | * | 7/2001 | Bawa et al. ................. 424/78.04 |
| 6,368,618 | B1 |  | 4/2002  | Jun et al. |
| 6,464,986 | B1 |  | 10/2002 | Aoki et al. |
| 2004/0047807 | A1 | | 3/2004  | Meyer |

FOREIGN PATENT DOCUMENTS

DE     195 45 180 A1     6/1997

OTHER PUBLICATIONS

Milligan et al. Anaesthesia 1988, 43, 563-564.*
Strichartz (Regional Anesthesia and Pain Medicine 1998, 23(1), 3-6).*
WO 00/61152, Management of Pain After Joint Surgery, Publication Date: Oct. 19, 2000.
WO 02/00172, Methods for Using Tetanus Toxin for Benificial Purposed in Animals (Mammals), Publication Date: Jan. 3, 2002.
Cruwys, S.C. et al.; "Sensory denervation with capsaicin attenuates inflammation and nociception in arthritic rats"; Neuroscience Letters; 1995; pp. 205-207; vol. 193, No. 3; Elsevier Science Ireland Ltd.; Limerick, Ireland; XP001013442.
Calvillo, O. et al.; "Neuroaugmentation in the Management of Sacroiliac Joint Pain: Report of Two Cases"; SPINE; May 1, 1998; pp. 1069-1072; vol. 23, No. 9; Lippencott-Raven Publishers; Philadelphia, Pennsylvania; XP001013345.
Ulseth E., "Nerve blocks for chronic pain"; Database EMBASE Online; Database accession No. 79200943; 1998; Elsevier Science Publishers, Amsterdam, Netherlands & 1979; pp. 930-932, 955; Tidsskrift for den Norske Laegeforening, Norway; XP002232748.

* cited by examiner

*Primary Examiner* — Ernst V Arnold
(74) *Attorney, Agent, or Firm* — Rankin, Hill & Clark LLP

(57) ABSTRACT

The invention relates to using neurotoxic substances which in particular are toxic to the axons and to the nociceptive nerve endings in the preparations of agents treating joint pains.

33 Claims, No Drawings

USE OF NEUROTOXIC SUBSTANCES FOR THE PRODUCTION OF A MEANS FOR THE TREATMENT OF JOINT PAINT AND METHOD FOR APPLICATION OF SAID MEANS

This application is a §371 of PCT/CH02/00400, filed on Jul. 19, 2002.

The present invention relates to the use of neurotoxic substances for the preparation of an agent for treating joint pain and a method for applying this agent into the intracapsular space or into the synovial sac of the joint.

Pain emanating from joints often originates in the area of the joint capsule or in the bone area close to the joint. This may involve many etiologies such as, for instance, arthrotic or arthritic diseases, mechanical or other irritation of the bone surface near the joint, infections, autoimmune processes, etc. In all cases of interest for the purpose of the present invention, the developing pain emanates from nociceptive nerve fibers in the area near the joint. Nociceptive nerve fibers are also called C-fibers and A-delta fibers. If an analgesic substance (such as local anesthetics of morphine) is injected into such a diseased joint, the patient's symptoms are alleviated. However, the effect of the most common substances today is of only limited duration, and the pain usually recurs.

Today, the following procedures are generally used for treating painfully-diseased joints:
  Physiotherapy/motion therapy
  Systemic analgesic/anti-inflammatory therapy (etc.)
  Local analgesic/anti-inflammatory procedures (etc.)
  Surgical procedures
  Arthroscopic: debridement, joint cleaning, etc.
  Open/mini-open: joint replacement, joint stiffening, etc.

In the literature, a series of known substances for treating painful, inflammatory joints have been recommended, in particular:
  Osmic acid or radioactive substances such as technetium 99, which resulted in synoviorthesis;
  Injection of local anesthetics, hyaluronic acid preparations (etc.)
  Injection of antiinflammatories
  Injection of contrast agents for joint diagnostics
  Joint flushing for cleansing joint
  Chemical, thermal, electrical or surgical ablation of the nerves supplying the joint.

All substances and procedures used until now lead to only a relatively short or incomplete freedom from pain, or cause long-lasting damage to the joint.

For instance, the known synoviorthesis method has the disadvantage of denaturing the structures, in particular the proteins, which act as inflammation triggers in the developmental process of arthritis and, in part, of arthrosis. This creates a fibrosis of the joint capsule that is less inflammatory and therefore less painful. At the same time, the fibrosis occurring during synoviorthesis of the joint reduces the usually-present hyperemia, which also needs to be treated, resulting in a therapeutic benefit as well. The fibrotic post-synoviorthesis scarring, however, may also lead to reduced mobility of the joint, as well as to reduced production of synovial fluid. This undesired fibrosis of the joint capsule should be prevented, and only the sensory innervation of the joint should be eliminated.

This is where the present invention comes in. The object of the invention is to search for suitable substances and to develop a method for injecting such substances, which longlastingly damage the nerve ends responsible for nociception for long-term analgesia, without endangering structures distant from the joint.

The method of the present invention consists in injecting a neurotoxic, neurolytic and neuroparalytic or long-term analgesic substance (hereafter, and in particular in the claims, termed generically as a "neurotoxic" substance) into a painful or ailing joint of the human or animal body. This substance may be left in place or be evacuated in part or in whole after a given time of action. When introduced, the therapeutic substance diffuses to the sensitive nerve endings which directly or indirectly innervate the region of the joint, and it predominantly inhibits or damages these nerve endings, and in this manner it reduces the perception of joint pain. It is known that local anesthetics are locally anesthetic only for a short time. However it was surprisingly found that solutions of high concentrations may act selectively neurolytically upon being inserted into the joint cavity (neurotoxic effect). Moreover the method of the invention is novel in that the joint capsule or the synovial pouch are being used for the purpose of concentrating the action of the therapeutic substance on the site of pain generation, making it possible in this manner to locally increase the therapeutic substance concentration more than would be possible in the absence of the protective joint capsule or the synovial pouch at the same concentration and compatibility while simultaneously leaving relatively unaffected the cavity/nerve structures and other structures near the joint. Long-term alleviation of pain perception due to the diseased fascicle-capsule-joint complex is attained by inhibiting or eliminating transmission of irritation. This method may be carried out both preventatively or therapeutically. At the same time the disinfecting effect of the neurotoxic substance kills off potential infecting pathogens, a circumstance which also may be exploited therapeutically.

The following advantages of employing the neurotoxic substances in the manner of the invention and of the method of the present invention injecting said substances into the joint capsule or into the joint synovial pouch are attained:
  Intraarticular injection of selective, neurotoxic substances to analgesically treat joints substantially preserves from harm the capsule-fascicle structures of the synovia and of the cartilage-bone structures and hence allows preserving the physiological conditions;
  Using the joint capsule as the natural boundary when spreading a neurotoxic substance;
  The action of the neurotoxic substances does not depend on specific neuronal epitopes;
  The method of the present invention may be carried out by non-specialists;
  The method of the present invention also may be carried out using a thin, non-arthroscopic needle;
  The method of the present invention does not entail danger of infection, contrary to the popular procedure of cortisone injection which entails pronounced local infection because cortisone locally inhibits the immune system;
  The method of the present invention entails significant denervation, that is bypassing pain-conducting nerves;
  Broadening joint mobility by eliminating painful mobility restriction contrary to the case of synoviorthesis wherein the resulting capsule fibrosis leads to mobility restriction;
  Positive preparation for subsequent arthroplasty. Because of the sclerotizing effect of the neurotoxic substance (on one hand due to a chemical-biological resection, on the other hand due to the mechanical stress during painful joint use), the bone near the joint acquires a structure which is advantageous to subsequently support a prosthesis;

No local fatty tissue resorption (lipolysis)

No weakening of collagenous tendon/fascicle/capsule structures.

The invention is discussed below as applied to humans, and in particular the stated dosages relate to human application. Nevertheless the present invention also is appropriate for veterinary purposes, where the dosages must be matched to the body weight of the particular animal.

Local anesthetics were found especially well suited to prepare agents for treating joint pains. Highly concentrated local anaesthetics which still are in the form of standard doses (alone or preferably in combination), were found particularly effective, for instance:

Lidocaine, preferably at a concentration of more than 6%, the maximum dose being 500 mg; prilocaine, preferably at a concentration of more than 3%, the maximum dose being 600 mg; mepivacaine, preferably at a concentration of more than 5%, the maximum dose being 500 mg; bupivacaine, preferably at a concentration of more than 1.5%, the maximum dose being 150 mg;

Levobupivacaine, preferably at a concentration of more than 5%;

Ropivacaine, at a concentration of more than 2%;

Etidocaine, preferably at a concentration of more than 2%, maximum dose being 300 mg; procaine, preferably at a concentration of more than 3%, maximum dose being 600 mg; chloroprocaine, preferably at a concentration of more than 3%, maximum dose being 800 mg; levobupivacaine, preferably at a concentration of more than 5%;

Ropivacaine at a concentration more than 2%;

Etidocaine, preferably at a concentration of at least 2%, maximum dose being 300 mg; procaine, preferably at a concentration of more than 3%, maximum dose being 600 mg; chloroprocaine, preferably at a concentration of more than 3%, maximum dose being 800 mg.

Tetracaine, preferably at a concentration of more than 4%, maximum dose being 100 mg.

Moreover the lidocaine compounds, for instance lidocaine (8%) and its compounds in high concentrations.

Mixtures of two or more neurolytic substances were found to be especially effective. Illustratively the combination of two local anesthetics, a local anesthetic with a bisulfite (for instance sodium bisulfite or potassium bisulfite) or for instance a cresol, or the combination of two local anesthetics with a bisulfite and/or a cresol etc.

When using local anesthetics as the neurotoxic substance, acid additives were found to be potentiating, for instance $NaHSO_3$ being added to chloroprocaine. In this manner the pH value is lowered to about 3, resulting in enhancing the effect of the invention implemented by the local anesthetic.

The above listed groups of substances are characterized by the following advantageous properties:

long-term action
optional one-time application
systemically non-toxic at the effective dose
predominantly neurotoxic/neurolytic to sensitive fibers, less for proprioceptive fibers and motor fibers
rapid action
non-toxic for synovia
non-toxic for bones
non-toxic for ligaments
non-toxic for cartilage
non-toxic for blood vessels
painless at injection
little or reversibly injurious when exiting the joint capsule
soluble and injectable
miscible with the desired additives
recovery possible in case of motor neuron lesions
does not contribute to inflammation
germicidal In a special implementation of the present invention, addition of phenol and phenol derivatives, inclusive analogues and pharmacologically acceptable salts among which local anesthetics, was found advantageous. Foremost among the phenol derivatives, the cresols, in particular ortho-, meta- and para-cresols and their derivatives, were found being effective. Among the cresol derivatives the chlorocresols, in particular 2-chloro-m-cresol, 3-chloro-p-cresol, 4-chloro-m-cresol, 3-chloro-o-cresol, 6-chloro-o-cresol, 2-chloro-p-cresol, 5-chloro-o-cresol, 6-chloro-m-cresol and 4-chloro-o-cresol are most suitable.

In one preferred implementing mode of the present invention, an x-ray contrasting agent such as a barium additive or an MRI contrasting agent is used in addition to the neurotoxic substance, making possible image monitoring the neurotoxic substance's distribution in the intracapsular space.

Depending on the procedure, the following substances may be used as contrasting agents:

x-rays, CT: iodine-holding substances such as tri-adapted benzoates or lopamidol, ideally 30-80 g/100 ml, or for instance 5-10% of another contrast agent such as barium,
MRI: for instance gadolinium, illustratively per 1 ml: 469.01 mg gadopentate dimeglumide, 0.99 mg meglumine, 0.4 mg diethyltriamine-pentaacetate.

In a further preferred mode of implementing the present invention, an antibiotic, disinfecting and/or sterilizing substance is added to the neurotoxic substance.

In a further preferred implementing mode of the present invention, a viscous additive such as hyaluronic acid preferably at a concentration of 0.1-10.0 mg/ml of injection solution is used in addition to the neurotoxic substance, attaining thereby improved mechanical joint gliding.

In a further preferred implementing mode of the present invention, a vaso-constricting substance such as Adrenalin, Noradrenalin or other, similar, preferably alpha adrenergic vasoconstrictors are used in addition to the neurotoxic substance. When Adrenalin is used, the total neurotoxin dose (as regards the toxic substance for the peripheral system) may be increased approximately by a factor of 2 because thereby the systemic effect is reduced by the lesser resorption. The concentration of Adrenalin may be 1/10,000 to 1/80,000 to 1/200,000. The total dose of Adrenalin is <0.25 mg. A 50 ml solution of 1/200,000 Adrenalin contains 0.25 mg Adrenalin.

In yet another preferred mode of implementation of the present invention, an anti-phlogistical substance, for instance non-steroidal anti-rheumatic agents such as COX-2 inhibitors, acetyl salicylic acid etc., is used in addition to the neurotoxic substance.

In still another preferred mode implementing the present invention, a steroid is used in addition to the neurotoxic substance in order to monitor/control any inflammatory reaction. This feature furthermore allows adding a rather causal treatment of painful, inflammatory joint diseases to support the symptomatic, neurolytic therapy. Betamethasone, for instance 5 mg of betamethasone in the form of diproprionate (crystalline suspension) and 2 mg betamethasone in the form of disodium phosphate (solution in 1 ml that may be added to the total quantity to be injected) was found especially appropriate. This solution is equivalent to 45/23 mg of prednisone/prednisolone.

In another preferred mode implementing the present invention, glycerin is added as solvent to the neurotoxic substance. Glycerin also exhibits neurotoxic properties (in particular when injected intraneurally). Glycerin furthermore lubricates the joint and accordingly exhibits a physical effect. Preferably the glycerin concentration is between 10 and 95%.

In a further preferred implementing mode of the present invention, an analgesic is added to the neurotoxic substance to induce short-term analgesia in the event the neurotoxic effect should be delayed and thereby an initial, painful time interval would set in. However highly concentrated local anesthetics in standard doses were found especially efficient, for instance the other substances cited above.

Instead of glycerin, the solvent also may be in the form of water, cooking salt solution, sodium iothalamate, iophendylate, ricin, polyethylene glycol or propylene glycol. The advantage of using glycerin as the solvent is its hyperbaric nature and also being already slightly neurotoxic per se.

Several substances were found to be potiating for the neurotoxic substances, for instance anti-oxidants, preservatives and excipients, in particular sodium bisulfite (>0.2%), $NaHSO_3$, ammonium compounds such as ammonium sulfate $(NH_4)_2SO_4$, 2-10 (~30%) polysorbate 80 (PS80) 0.025 mg/ml.

Preferably the neurotoxic substance is dissolved in a biocompatible solvent and is appropriately injected in a volume matching the available space in the joint being treated in a manner that said joint shall be filled to bursting. In this manner the neurolytic substance is advantageously optimally distributed. However less liquid may be injected, in which case however the joint must be moved sufficiently to attain improved neurolytic substance distribution.

The volume of liquid to be injected into the intracapsular space may be from 0.1 to 150 ml. An approximate maximum of 1 ml suffices for the finger joint, about a maximum of 10 ml for the shoulder joint, and about 30 to 50 ml for the knee joint.

Dosing the neurolytic substance depends on its absolute solubility in the selected solution medium. The capsule thickness of the particular joint substantially affects the dosing. The thicker the capsule, the larger the required concentration or quantity of the neurolytic substance.

When using chloro-cresol as the neurolytic substance in glycerin as the biocompatible solvent, an appropriate quantitative ratio of chloro-cresol to glycerin of 1:5 to 1:70, preferably 1:40 to 1:50, should be selected.

When using phenol in glycerin, an appropriate range of concentrations of 0.5 to 40.0%, preferably 3-12% should be selected.

An additive to the neurotoxic substance enhancing permeation, for instance dimethyl sulfoxide, was found advantageous.

Several illustrative modes of implementation are discussed below to elucidate the present invention.

EXAMPLE 1

Checking by optional, simultaneous image generation (image transducer, CT, sonography, MRI etc.) or by delayed image generation (x-rays, CT, sonography, arthroscopy etc.), the therapist inserted an injection needle into the joint space of a knee joint and injected 40 ml of a solution of 8% tetracaine, 16% lidocaine and 1% m-chloro-cresol in glycerin into the intracapsular space. Already 14 h following intervention, patient already experienced clear alleviation of complaint. This alleviation lasted more than 6 months.

EXAMPLE 2

Checking by optional, simultaneous image generation (image transducer, CT, sonography, MRI etc.) or by delayed image generation (x-rays, CT, sonography, arthroscopy etc.), the therapist inserted an injection needle into the joint space of a knee joint and injected 20 ml of a solution of 0.8% sodium bisulfite into the intracapsular space. Already a few days following intervention, the patient felt substantial alleviation of complaints. Said alleviation lasted more than 6 months.

EXAMPLE 3

The injected solution was that of Example 1 except that 5 ml of a visible contrasting agent (lopamidol at a concentration of 50 g/100 ml) was added for the image generating procedure, said agent upon injection spreading inside the joint capsule and in this manner revealing the position of the injection needle and the distribution of the therapeutic substance within the capsule. Immediately upon completion of injection, the neurotoxic substance contained into the injected solution was aspirated out again. However said substance also might be withdrawn following a given exposure time determined by the particular substance, or not at all. Already 15 h following intervention, patient was aware of significant alleviation of complaints. Said alleviation lasted longer than 8 months.

EXAMPLE 4

The therapist inserted a thin infusion catheter similar to an epidural catheter into the ailing joint and, using a perfusor, injected a mixture of 5% tetracaine, 12% lidocaine, 2% chloro-cresol, 5% hydrocortisone, 10% contrasting agent and 66% glycerin into said joint at a rate of 1-10 ml/h for 12 h. Optionally he also inserted a draining catheter exhibiting a defined drainage impedance (for instance 20 mm Hg) for purposes of liquid replacement. In this manner therapist attained uniform infiltration, i.e. free of large peaks of concentration, of the painful joint. Also the time of exposure could be defined more accurately.

Subsequent arthroscopy after 1, 2, 7, 14 and 28 days showed only minimal infected tissue being present. Already 12 h following intervention, patient experienced substantial alleviation of complaints. This alleviation lasted more than 1 year.

EXAMPLE 5

Following implantation of a knee joint prosthesis, therapist injected 50 ml of a mixture of 7% tetracaine, 15% lidocaine and 5% chloro-cresol in glycerin into the resealed joint capsule. As a result the post-surgery pains could be minimized.

EXAMPLE 6

Following implantation of a hip joint prosthesis, the therapist injected 50 ml of a mixture of 8% tetracaine, 16% lidocaine and 5% chloro-cresol in glycerin into the periprosthetic region without a capsule. In this manner the post-surgery pains could be minimized.

EXAMPLE 7

The neurotoxic substance (in this instance: 8% tetracaine, 16% lidocaine and 5% chloro-cresol in glycerin) was injected into the (neo)-capsule around the prosthesis of a patient suffering from septic loosening of the hip total endoprosthesis, whereupon this patient experienced long-term (>1 year) pain alleviation within a few (6-12) hours. Moreover the infection around the prosthesis was strongly controlled by the diffusion of the neurotoxic substance (which also acted antiseptically) along the prosthetic stem and around the socket and in some cases it could be eliminated entirely. Such treatment may be optionally supported with systemically administered antibiotics (for instance 450 mg rifampicin, 750 mg ciprofloxacin).

Consolidation of the bone substance around the prosthesis was shown radiologically.

EXAMPLE 8

Checking by optional, simultaneous image generation (image transducer, CT, sonography, MRI etc.) or by delayed image generation (x-rays, CT, sonography, arthroscopy etc.), the therapist inserted an injection needle into the joint space of a knee joint and injected 40 ml of a solution of 20% lidocaine mixed with 0.6% sodium bisulfite in physiological cooking salt solution into the intra-capsular space. Already a few minutes after intervention, patient experienced substantial alleviation of complaints. This alleviation lasted more than 6 months.

EXAMPLE 9

Checking by optional, simultaneous image generation (image transducer, CT, sonography, MRI etc.) or by delayed image generation (x-rays, CT, sonography, arthroscopy etc.), the therapist inserted an injection needle into the knee joint space and injected 20 ml of a solution of 1% bupivacaine mixed with 6% tetracaine in physiological cooking salt solution into the intra-capsular space. Already minutes after intervention patient experienced significant alleviation of complaints. This alleviation lasted more than 6 months.

EXAMPLE 10

Checking by optional, simultaneous image generation (image transducer, CT, sonography, MRI etc.) or by delayed image generation (x-rays, CT, sonography, arthroscopy etc.), the therapist inserted an injection needle into the knee joint space and injected 20 ml of a solution of 15% lidocaine mixed with 1% bupivacaine and 0.6% sodium bisulfite in physiological cooking salt solution into the intra-capsular space. Already a few minutes after intervention, patient experienced significant alleviation of complaints. This alleviation lasted more than 6 months.

EXAMPLE 11

Checking by optional, simultaneous image generation (image transducer, CT, sonography, MRI etc.) or by delayed image generation (x-rays, CT, sonography, arthroscopy etc.), the therapist inserted an injection needle into the joint space of a knee joint and injected 20 ml of a solution of 4% tetracaine mixed with 3% chloro-cresol and 0.6% sodium bisulfite in a physiological cooking salt solution into the intra-capsular space. Already a few minutes following intervention, patient felt substantial alleviation of complaints. This alleviation lasted more than 8 months.

EXAMPLE 12

A mixture of 8% tetracaine and 2% chloro-cresol in physiological cooking salt solution was injected into the joint of a patient suffering from painful joints capsulitis (for instance "frozen shoulder"). An antiphlogistically effective substance was admixed optionally. A few minutes following injection, the pains abated long-lastingly, so that the patient taking physical therapy regained the mobility that had been lost by capsulitis. A transient analgesia (2-3 weeks) is sometimes desirable in this application and for that reason in this instance the neurotoxic substance concentration was kept rather low.

EXAMPLE 13

A mixture of 8% tetracaine and 16% lidocaine in physiological cooking salt solution was injected into the joint of a patient suffering from painful joints capsulitis. A few minutes after injection, the pains abated long-lastingly as a result of which, with physical therapy, the patient regained the mobility that had been lost due to capsulitis.

EXAMPLE 14

A mixture of 16% lidocaine and 3% chloro-cresol in physiological cooking salt solution was injected into the joint of a patient suffering from painful joints capsulitis. The pains abated long-lastingly a few minutes following injection, and patient undergoing physical therapy regained the mobility that had been lost due to capsulitis.

EXAMPLE 15

The therapist injected 5 ml of a neurotoxic substance composed of 8% tetracaine, 8% chloro-cresol and 40 mg cortisone in glycerin as the solvent into a chronically inflamed bursa trochanterica through the trochanter major of the hip. Within 60 minutes, patient's complaints disappeared and remained absent for several years.

EXAMPLE 16

The therapist injected 5 ml of a neurotoxic substance composed of 12% lidocaine, 7% chloro-cresol and 40 mg cortisone in glycerin as solvent into a chronically inflamed bursa trochanterica through the hip's trochanter major. Complaints of patient disappeared within 60 minutes and remained absent at this site for several years.

EXAMPLE 17

The therapist injected 1 ml of a neurotoxic substance composed of 15% lidocaine, Adrenalin (1/10,000 of total solution) and 5% contrast agent in physiological cooking salt solution as solvent into a painful, arthrotic finger joint. After 15 minutes, patient's complaints disappeared for several months. Proper injection needle position could be checked by the contrast agent.

EXAMPLE 18

The therapist injects a mixture composed of 5% chloro-cresol, 10% lidocaine and vincristine in a quantity of 0.7 mg in glycerin as the solvent. This mixture exhibits especially long-term effectiveness because its components damage in different ways the nerves to be damaged. The action of chloro-cresol dissolves the nerve membrane, that of lidocaine destroys the nerves by irreversible receptor blocking as well as by toxic, intracellular release of Ca, and that of vincristine by long-lastingly preventing nerve regeneration and inhibiting axonal transport.

EXAMPLE 19

The therapist injects a mixture of 5% chloro-cresol, 10% lidocaine, 0.7 mg of vincristine, Adrenalin (1/15,000 of total solution) and 10% contrast agent in glycerin as the solvent. This mixture was found especially effective for long-lasting nerve destruction.

The invention claimed is:

1. A method for treating post-operative joint pain, the method comprising:
   providing an agent for treating joint pain comprising a neurotoxic substance dissolved in a bio-compatible solvent, wherein said neurotoxic substance is an amide local anesthetic, and wherein said amide local anesthetic is present in said agent for treating joint pain in a concentration whereby said agent for treating joint pain is predominantly toxic to nociceptive nerve fibers but not systemically toxic when injected into a post-operative joint space; and
   injecting the agent for treating joint pain into said post-operative joint space as a one time application in an amount sufficient to entail neurolysis.

2. The method as claimed in claim 1, wherein the amide local anesthetic is less neurotoxic to motor and propioceptive nerve fibers than to sensitive nerve fibers.

3. The method as claimed in claim 1, wherein the amide local anesthetic is used at a concentration larger than 4%.

4. The method as claimed in claim 1, wherein the amide local anesthetic is used jointly with a pH-lowering additive.

5. The method as claimed in claim 4, wherein the pH-lowering additive is a bisulfite.

6. The method as claimed in claim 5, wherein the pH-lowering additive is sodium bisulfite ($NaHSO_3$).

7. The method as claimed in claim 4, wherein the pH-lowering additive is used at a concentration of at least 1% by weight.

8. The method as claimed in claim 4, wherein the pH-lowering additive lowers the pH of the agent for treating joint pain to less than 3.5.

9. The method as claimed in claim 4, wherein the amide local anesthetic is lidocaine at a concentration larger than 6%.

10. The method as claimed in claim 4, wherein the amide local anesthetic is prilocaine at a concentration larger than 3%.

11. The method as claimed in claim 4, wherein the amide local anesthetic is mepivacaine at a concentration larger than 5%.

12. The method as claimed in claim 4, wherein the amide local anesthetic is bupivacaine at a concentration larger than 1.5%.

13. The method as claimed in claim 4, wherein the amide local anesthetic is levobupivacaine at a concentration larger than 5%.

14. The method as claimed in claim 4, wherein the amide local anesthetic is ropivacaine at a concentration larger than 2%.

15. The method as claimed in claim 4, wherein the amide local anesthetic is etidocaine at a concentration larger than 2%.

16. The method as claimed in claim 4, wherein the amide local anesthetic is used in pure, enantiomeric form.

17. The method as claimed in claim 4, wherein a phenol or a pharmacologically acceptable phenol salt is used in addition to the amide local anesthetic.

18. The method as claimed in claim 17, wherein the phenol derivative is a cresol.

19. The method as claimed in claim 18, wherein the cresol is a chloro cresol selected from the group consisting of 2-chloro-m-cresol, 3-chloro-p-cresol, 4-chloro-m-cresol, 3-chloro-o-cresol, 6-chloro-o-cresol, 2-chloro-p-cresol, 5-chloro-o-cresol, 6-chloro-m-cresol and 4-chloro-o-cresol.

20. The method as claimed in claim 17, wherein the phenol derivative is a eugenol.

21. The method as claimed in claim 17, wherein the phenol derivative is a thymol.

22. The method as claimed in claim 1, wherein the agent for treating joint pain further comprises an x-ray contrast agent that contains gadolinium, iodine or barium in addition to the neurotoxic substance.

23. The method as claimed in claim 1, wherein the bio-compatible solvent is glycerin, and wherein the glycerin is used at a concentration of 10 to 95% by wt in addition to the neurotoxic substances.

24. The method as claimed in claim 1, wherein steroids are used in addition to the neurotoxic substance.

25. The method as claimed in claim 1, wherein a vasoconstrictor selected from the group consisting of adrenaline, noradrenaline, phenylephrine and ornipressine, is used in addition to the neurotoxic substance.

26. The method as claimed in claim 1, wherein the neurotoxic substance is dissolved in a biocompatible solvent selected from the group consisting of glycerin, iophendylate and propyleneglycol.

27. The method as claimed in claim 1, wherein the agent further comprises dimethyl sulfoxide as a permeation enhancer.

28. The method as claimed in claim 1, wherein an analgesic is added to the neurotoxic substance.

29. The method as claimed in claim 1, wherein the bio-compatible solvent is polyethylene glycol.

30. A method for treating post-operative joint pain, comprising:
   injecting an agent comprising a neurotoxic substance dissolved in a bio-compatible solvent into the intra-capsular region or into the joint synovial pouch of the pain-afflicted joint as a one time application at a concentration entailing neurolysis, wherein the neurotoxic substance is an amide local anesthetic and is present in said agent in a concentration whereby said agent is predominantly toxic to nociceptive nerve fibers but not systemically toxic.

31. The method for treating joint pain as claimed in claim 30, wherein the neurotoxic substance is a mixture of several amide local anesthetics and wherein a liquid volume of 0.1 to 150 ml of the agent is injected into the intra-capsular region or into the joint synovial pouch of the pain-afflicted joint.

32. The method as claimed in claim 31, wherein the nociceptive nerve fibers are rendered pain-insensitive by the mixture of several amide local anesthetics for at least 14 days.

33. The method as claimed in claim 30, wherein the nociceptive nerve fibers are rendered pain-insensitive by a mixture of several amide local anesthetics for at least 14 days.

* * * * *